United States Patent [19]
Gonze et al.

[11] Patent Number: 5,261,270
[45] Date of Patent: Nov. 16, 1993

[54] FUEL COMPOSITION SENSOR DIAGNOSTIC APPARATUS

[75] Inventors: Eugene V. Gonze, Sterling Heights, Mich.; John K. Orminski, Ontario, Canada; Larissa C. Chu, Kokomo, Ind.

[73] Assignees: General Motors Corporation, Detroit, Mich.; Delco Electronics Corporation, Kokomo, Ind.; General Motors of Canada Ltd., Oshawa, Canada

[21] Appl. No.: 745,624

[22] Filed: Aug. 15, 1991

[51] Int. Cl.$^5$ .................... G01N 27/22; G01N 33/22; F02M 51/00; F02M 7/00

[52] U.S. Cl. .................... 73/61.43; 73/53.01; 123/1 A; 123/494; 324/663; 324/685

[58] Field of Search .................... 73/61.43, 61.44, 61.59, 73/53; 324/663, 685; 361/280, 281; 123/494, 1 A

[56] References Cited

U.S. PATENT DOCUMENTS

| | | | |
|---|---|---|---|
| 4,470,300 | 9/1984 | Kobayashi | 73/304 C |
| 4,706,629 | 11/1987 | Wineland et al. | 123/478 |
| 4,909,225 | 3/1990 | Gonze et al. | 123/494 |
| 4,939,467 | 7/1990 | Noglami et al. | 324/663 |
| 4,939,468 | 7/1990 | Takeuchi | 324/690 |
| 4,945,880 | 8/1990 | Gonze et al. | 123/494 |
| 4,945,885 | 8/1990 | Gonze et al. | 123/520 |
| 4,957,087 | 9/1990 | Ota | 123/494 |
| 4,995,367 | 2/1991 | Yamauchi et al. | 123/1 A |
| 5,103,184 | 4/1992 | Kapsokavathis | 324/663 |

OTHER PUBLICATIONS

Hile et al, "An On-Board Sensor for Percent Alcohol", *IEEE Transactions on Vehicular Technology*, vol. VT-27, No. 3, Aug. 1978.

Schmitz et al, "Intelligent Alcohol Fuel Sensor", *SAE Paper No. 900231*, Society of Automotive Engineers, 1990.

Primary Examiner—Hezron E. Williams
Assistant Examiner—George M. Dombroske
Attorney, Agent, or Firm—Robert M. Sigler

[57] ABSTRACT

A motor vehicle fuel composition sensor is responsive to a dielectric constant of a mixture of two fuels such as gasoline and methanol to indicate the relative concentrations of each. The sensor is fuel temperature dependent at high concentrations of methanol; and a fuel temperature sensor thus provides a fuel temperature signal for fuel composition signal correction. Diagnostic apparatus stores references defining permissible operating ranges for the fuel temperature and fuel composition sensor outputs and compares the sensor outputs with these ranges to detect abnormal sensor operation. The reference defining the end of the fuel composition sensor range at maximum methanol, however, is corrected for fuel temperature if the fuel temperature sensor output is within range. An out of range signal from either sensor causes a default value to be substituted for fuel composition.

4 Claims, 3 Drawing Sheets

FUEL COMPOSITION SENSOR DIAGNOSTIC APPARATUS

BACKGROUND OF THE INVENTION

This invention relates to diagnostic apparatus for a fuel composition sensor of the type which is responsive to the dielectric constant of a mixture of two fuels to generate a fuel composition signal indicating the relative concentration of the two fuels. Such a sensor may be, for example, a capacitive sensor in which the fuel mixture to be sensed forms the dielectric between capacitor plates. If one of the fuels has a significant variation of dielectric constant with temperature, the output signal of such a sensor may vary with fuel temperature at high concentrations of the one fuel. In a fuel mixture of gasoline and methanol, for example, the output of such a sensor becomes significantly more dependent on fuel temperature as the concentration of methanol increases. Therefore, such a sensor may be provided with an accompanying fuel temperature sensor in the same package so that the fuel composition sensor output may be corrected for fuel temperature as required.

The diagnostic apparatus of the invention is of the type which detects failures such as a disruption of communication between the sensor(s) and an associated control responsive thereto by monitoring the fuel temperature sensor and fuel composition sensor outputs for values within predetermined allowed ranges. However, the diagnostic apparatus is desirably also used to detect contaminated fuel. Although a sensor will usually fail by shorting to one of the power supply terminals, in which case constant limit references may be acceptable, contaminated fuel may not produce such a pronounced failure. Rather, the contaminated fuel may produce an output voltage which, although outside the expected voltage range at a particular fuel temperature, is not at or near either of the voltage supply voltages. Therefore, to the extent that the fuel composition sensor output is temperature dependent, the use of a fixed allowed fuel composition range might provide an erroneous result where the temperature dependence is greatest: namely, for high concentrations of the one fuel, such as methanol, which exhibits a strong variation of dielectric constant with temperature.

SUMMARY OF THE INVENTION

The diagnostic apparatus of the invention comprises apparatus which stores a fuel composition sensor limit reference indicative of a limiting value for fuel composition sensor indicated concentration of one fuel in a fuel mixture at a predetermined fuel temperature. It further stores a temperature correction factor as a function of fuel temperature and is effective to derive a value of the temperature correction factor in response to the output of the fuel temperature sensor and generate a corrected fuel composition sensor limit reference by modifying the stored fuel composition limit reference in response to the derived value of the temperature correction factor. The apparatus compares the fuel composition sensor output with the corrected fuel composition sensor limit reference and, if the former exceeds the latter, substitutes a stored default fuel composition value for the former.

DESCRIPTION OF THE PREFERRED EMBODIMENT

Figure 1:
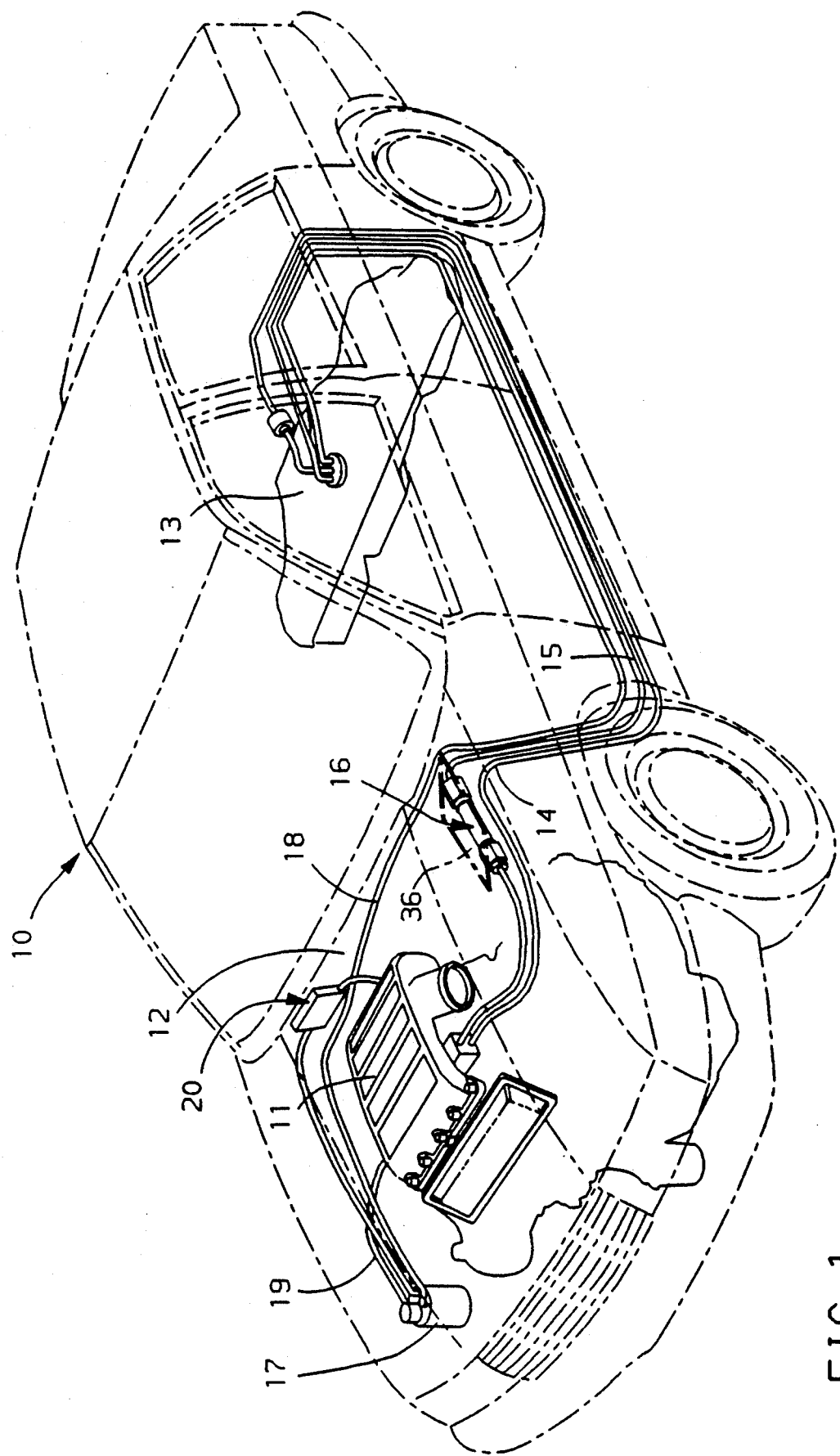
FIG. 1 shows a motor vehicle having fuel composition and temperature sensors and diagnostic apparatus according to the invention.
Figure 2:
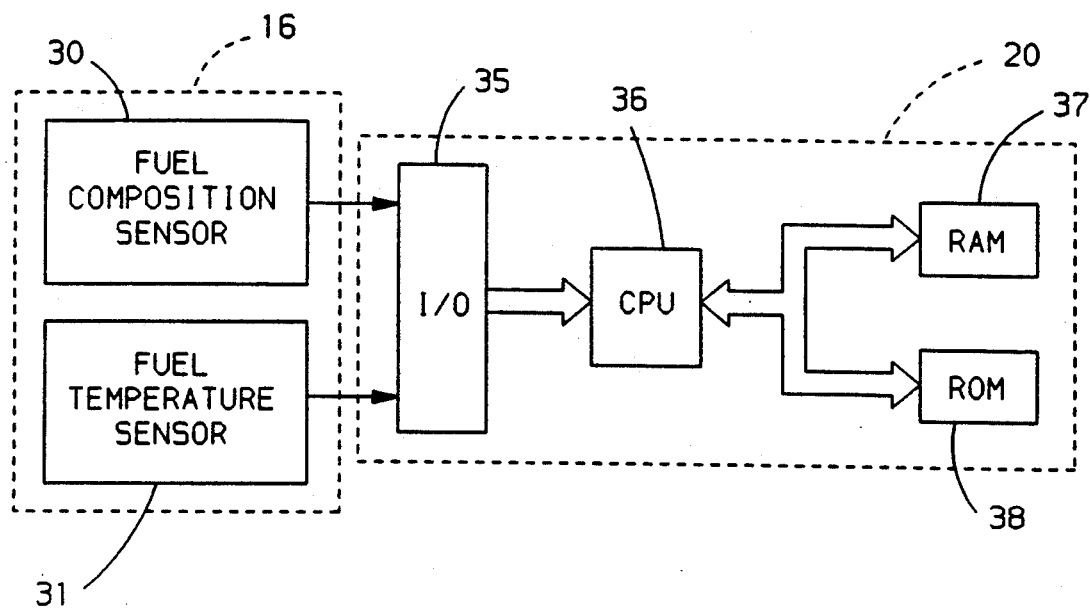
FIG. 2 is a block diagram of diagnostic apparatus for use in the vehicle of FIG. 1.

Referring to FIG. 1, a motor vehicle 10 is provided with an internal combustion engine 11 in an engine compartment 12, engine 11 receiving fuel from a fuel tank 13 at the opposite end of the vehicle through a fuel conduit 15 and returning excess fuel to tank 13 through fuel conduit 14. The fuel in tank 13 is a mixture of essentially two fuels, one of which is gasoline and the other of which is an alcohol such as methanol or ethanol. Fuel conduit 15 includes a fuel sensor package 16 located within engine compartment 12 at a point close to engine 11. As shown in FIG. 2, fuel sensor package 16 includes a fuel composition sensor 30 which generates a signal indicative of the relative proportion of alcohol to gasoline in the fuel flowing therethrough and further includes a fuel temperature sensor 31 providing a fuel temperature signal for correction of the fuel composition signal. Returning to FIG. 1, a standard fuel vapor collection canister 17 is connected by a vapor conduit 18 to fuel tank 13 for collection of vapor therefrom and another vapor conduit 19 to the induction system of engine 11.

The operation of engine 11 is controlled by an electronic controller 20, which may be located at the rear of the engine compartment as shown or any other convenient location. As shown in FIG. 2, controller 20 may comprise a programmed digital computer similar to those presently used in motor vehicles for engine control. The apparatus is well known, comprising a central processing unit (CPU) 36, RAM 37, ROM 38 and appropriate input/output (I/O) apparatus 35, with an appropriate program stored in ROM 38 to coordinate receipt of input information from various sensors, perform calculations and table look-ups and output commands to various actuators of engine related components. Controller 20 is responsive to the fuel composition signal from fuel composition sensor 30 as well as the fuel temperature signal from fuel temperature sensor 31, input thereto through I/O apparatus 35, to modify such engine operating parameters as the air/fuel ratio, ignition timing, canister purge rate and/or others as necessary to optimize engine operation for the actual fuel mixture provided to the engine as sensed by sensors 30 and 31.

This diagnostic apparatus makes use of several references stored in ROM 38 or RAM 37: maximum and minimum fuel temperature references which define between them a good fuel temperature range and maximum and minimum fuel composition sensor references which define between them a good fuel composition sensor output range. In the case of the fuel composition range, "maximum" and "minimum" refer to the concentration of the component of the fuel mixture, such as methanol, producing the greatest fuel temperature dependence in the fuel composition sensor output voltage. The appropriate sensor output voltages are compared with these references; however, the maximum fuel composition sensor reference is reduced with increasing fuel temperature as shown in curve 40 shown in FIG. 2.

Figure 3:
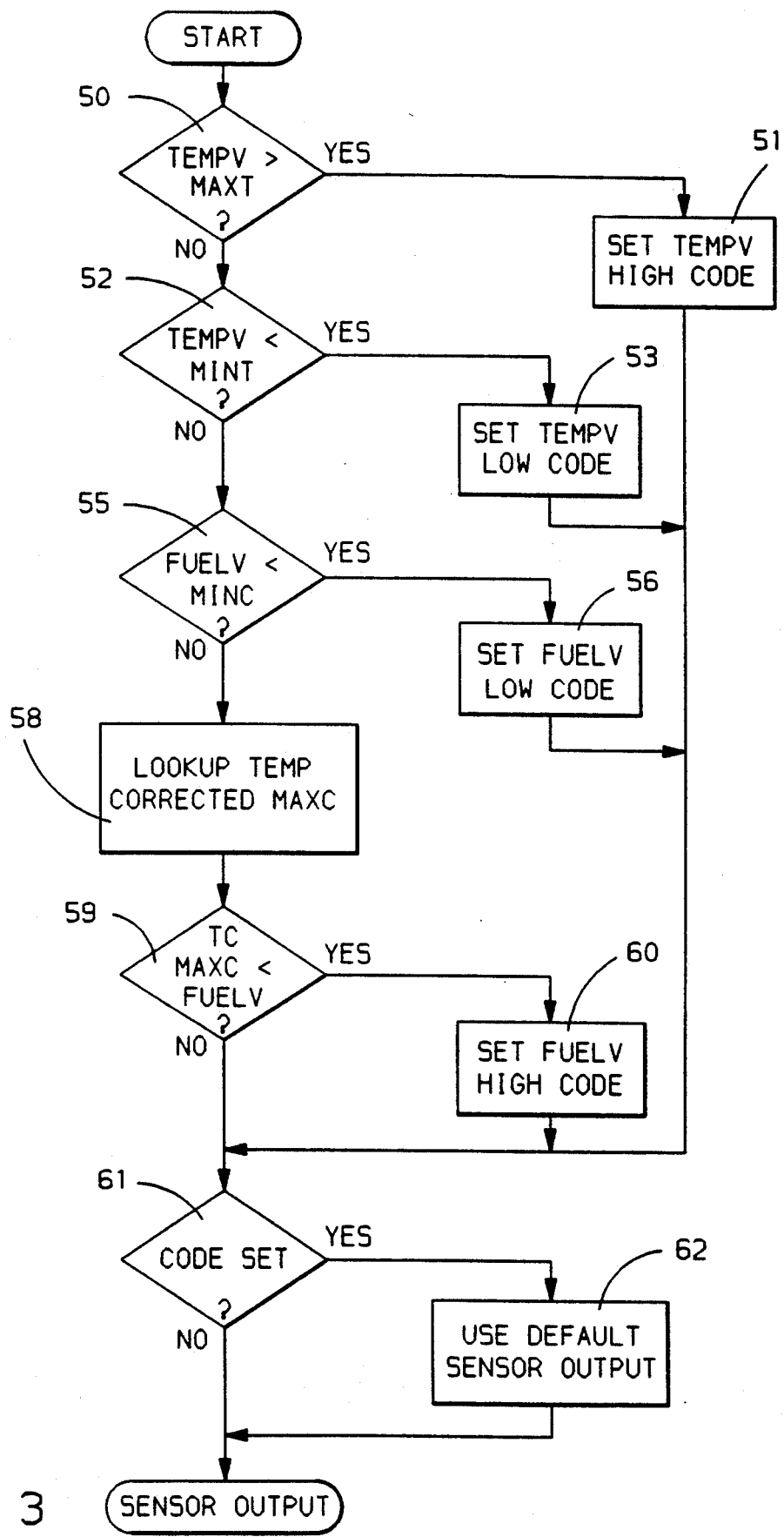
FIG. 3 shows a flow chart illustrating the operation of the diagnostic apparatus of FIG. 2.

FIG. 3 is a flow chart illustrating the operation of the diagnostic portion of the stored program referred to above. At decision point 50, the fuel temperature sensor output voltage TEMPV is compared with a maximum fuel temperature reference MAXT. If it exceeds this reference, it is out of range; and the program then sets a TEMPV HIGH diagnostic code at step 51. If the reference is not exceeded, however, the fuel temperature sensor output voltage is then compared with a minimum fuel temperature reference MINT at decision point 52. If it is lower than this reference, it is out of range; and a TEMPV LOW code is set in step 53.

If the fuel temperature sensor is within range, the fuel composition sensor output voltage FUELV is compared, at decision point 55, with a minimum fuel composition sensor limit reference MINC. In this embodiment, the minimum fuel composition sensor limit reference corresponds with minimum methanol concentration, or pure gasoline in a sensor having a voltage divider output taken across the variable, fuel composition sensitive capacitance. At this end of the fuel composition range, the fuel composition sensor output voltage is low and relatively insensitive to fuel temperature. Therefore, the stored minimum fuel composition sensor limit reference MINC is used unchanged. If the fuel composition sensor output voltage is lower than this reference, it is out of range; and a FUELV LOW diagnostic code is set in step 56. From any of steps 51, 53 or 56, the program proceeds to a decision point 61; and, since one of the diagnostic codes is set, a default fuel composition sensor output signal is substituted for the actual fuel composition sensor output voltage in step 62 before the fuel composition signal is output to the remainder of the control. This will occur if the fuel temperature sensor output voltage is out of range high or low or if the fuel composition sensor output voltage is out of range at the low methanol end of the fuel composition range.

If the sensor output voltages are found to be within range at decision points 50, 52 and 55, it only remains for the fuel composition sensor output voltage to be checked for out of range high. However, in this part of its range, the fuel composition sensor output voltage is most sensitive to fuel temperature. A maximum fuel composition sensor output voltage reference MAXC is stored in ROM or RAM; but this value corresponds to a predetermined low fuel temperature, such as −29 degrees C. With increasing fuel temperature, the maximum methanol output of the fuel concentration sensor decreases almost linearly with fuel temperature. Therefore, the apparatus stores in ROM 38 or RAM 37 a temperature correction factor as a function of fuel temperature. The preferred method for use with typical eight bit microprocessors is to store a plurality of values as a function of a fuel temperature input. A table lookup, with interpolation as required, is performed in step 58. An alternative approach, if the computer's floating point multiplication capability is strong, is to calculate the temperature corrected MAXC as the stored MAXC minus a constant times the fuel temperature TEMPV.

Figure 4:
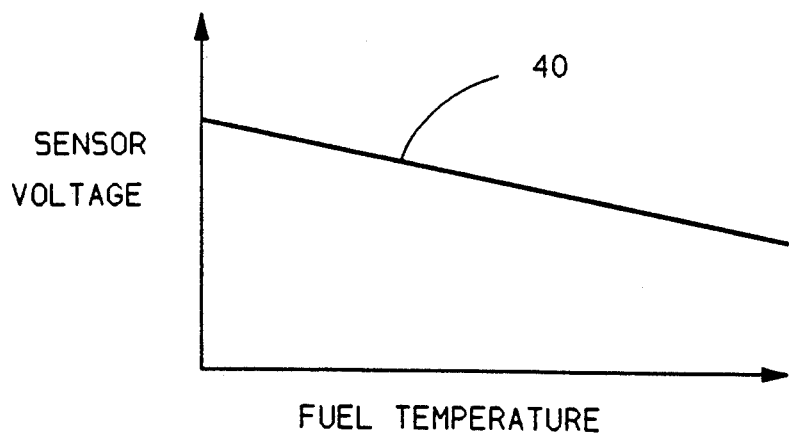
FIG. 4 shows a curve representing stored values of a fuel temperature correction factor as a function of fuel temperature for use in the apparatus of this invention.

Whichever method is chosen, the result may be similar to the curve shown in FIG. 4, which shows MAXC as a linearly decreasing function of fuel temperature from a high value at −29 degrees C. to a low value at 65 degrees C. If the lookup table approach is used, the output of fuel temperature sensor 31 is used as the lookup value, with interpolation as required for the desired accuracy. This step is followed by decision point 59, in which the fuel composition sensor output voltage is compared to the corrected maximum composition sensor reference. If it exceeds this reference, it is out of range; and a FUELV HIGH diagnostic code is set at step 60.

It should be noted that the fuel composition signal limit varied with fuel temperature is, in this embodiment, the maximum limit but may be, in certain other embodiments, the minimum limit, depending on the sensor circuitry. This embodiment assumes a voltage divider comprising a sensor capacitor in series with a constant reference capacitor with the output voltage taken across the sensor capacitor. If the output voltage is taken across the reference capacitor of the same voltage divider, however, or otherwise reversed in variation with fuel composition, the fuel composition signal limit varied with fuel temperature may be the minimum limit. Therefore, the language of the claims refers to a corrected fuel composition sensor limit reference and a fuel composition sensor output exhibiting a predetermined magnitude relative thereto. This means, for the embodiment described, a voltage exceeding a maximum limit and, for the opposite case, a voltage below a minimum limit.

At decision point 61, it is determined whether any diagnostic codes are set. If any are, a stored default value is substituted for the fuel composition sensor output voltage in step 62. In this embodiment, any diagnostic code being set sends the program immediately to decision point 61; and the same default is used regardless of the failure mode. It would be well within the ordinary skill of engine control designers, however, to modify the program so that the setting of any diagnostic code does not result in the skipping of the other tests; and the program ultimately chooses one from a plurality of stored default values depending on the particular combination of diagnostic codes set.

The embodiments of the invention in which an exclusive property or privilege is claimed are defined as follows:

1. A motor vehicle comprising, in combination:
   an engine capable of operating on a fuel mixture comprising a mixture of two fuels having different dielectric constants;
   a fuel tank for storing the fuel mixture;
   a conduit between the fuel tank and engine for delivering the fuel mixture from the fuel tank to the engine;
   a fuel composition sensor in the conduit responsive to a dielectric constant of the fuel mixture to indicate the relative concentrations of the two fuels, the sensor being fuel temperature dependent at high concentrations of one of the two fuels;
   an engine controller responsive to the fuel composition sensor for controlling the delivery of the fuel mixture to the engine;
   memory apparatus effective to store (1) a fuel composition sensor limit reference representing a limiting value for the sensor indicated concentration of the one fuel at a predetermined fuel temperature, (2) a temperature correction factor as a function of fuel temperature, and (3) a default fuel composition value;

diagnostic processor apparatus comprising (1) means for deriving a value of the temperature correction factor in response to the output of the fuel temperature sensor, (2) means for generating a corrected fuel composition sensor limit reference by modifying the stored fuel composition sensor limit reference in response to the derived value of the temperature correction factor, and (3) means for comparing the fuel composition sensor output with the corrected fuel composition sensor limit reference;

the engine controller being responsive to the diagnostic processor apparatus to substitute the default fuel composition value for the fuel composition sensor output if the fuel composition sensor output exhibits a predetermined magnitude relative to the corrected fuel composition sensor limit reference.

2. A motor vehicle according to claim 1 wherein the fuels are gasoline and methanol and the one of the fuels is methanol.

3. A motor vehicle comprising, in combination:
an engine capable of operating on a fuel mixture comprising a mixture of gasoline and alcohol;
a fuel tank for storing the fuel mixture;
a conduit between the fuel tank and engine for delivering the fuel mixture from the fuel tank to the engine;
a fuel composition sensor in the conduit responsive to a dielectric constant of the fuel mixture to indicate the relative concentrations of the two fuels, the sensor being fuel temperature dependent at high alcohol concentrations and high fuel temperature;
a fuel temperature sensor responsive to the temperature of the fuel mixture in the fuel composition sensor;
an engine controller responsive to the fuel composition sensor for controlling the delivery of the fuel mixture to the engine;
memory apparatus effective to store (1) maximum and minimum fuel temperature sensor references defining a good temperature sensor window therebetween. (2) a first alcohol fuel composition sensor limit reference, (3) a temperature correction factor as a function of fuel temperature, and (4) a default fuel composition value;

first diagnostic processor apparatus comprising means for comparing the fuel temperature sensor output with at least one of the maximum and minimum fuel temperature sensor references to determine whether the fuel temperature sensor output is within the good fuel temperature sensor window, the engine controller being responsive to the first diagnostic processor apparatus to substitute the default composition value for the fuel composition sensor output when the fuel temperature sensor output is not within the good fuel temperature sensor window; and second diagnostic processor apparatus comprising means effective only when the fuel temperature sensor output is within the good fuel temperature sensor window for (1) deriving a value of the temperature correction factor in response to the output of the fuel temperature sensor, (2) generating a corrected alcohol fuel composition sensor limit reference by modifying the stored alcohol fuel composition sensor limit reference in response to the derived value of the temperature correction factor, and (3) comparing the fuel composition sensor output with the corrected alcohol fuel composition sensor limit reference, the engine controller being responsive to the second diagnostic processor apparatus, if the fuel composition sensor output exhibits a predetermined magnitude relative to the corrected alcohol fuel composition sensor limit reference, substituting the stored default fuel composition value for the fuel composition sensor output.

4. A motor vehicle according to claim 3 in which the alcohol is methanol.

* * * * *